(12) United States Patent
Hollingsworth et al.

(10) Patent No.: US 8,193,309 B2
(45) Date of Patent: *Jun. 5, 2012

(54) COMPOSITIONS AND METHODS FOR PREVENTING OR TREATING CANCER

(75) Inventors: Michael Anthony Hollingsworth, Omaha, NE (US); Karl Kohlgraf, Iowa City, IA (US); Tom Caffrey, Bellevue, NE (US)

(73) Assignee: Board of Regents of the University of Nebraska, Omaha, NE (US)

( * ) Notice: Subject to any disclaimer, the term of this patent is extended or adjusted under 35 U.S.C. 154(b) by 83 days.

This patent is subject to a terminal disclaimer.

(21) Appl. No.: 12/696,603

(22) Filed: Jan. 29, 2010

(65) Prior Publication Data

US 2010/0190720 A1 Jul. 29, 2010

Related U.S. Application Data

(62) Division of application No. 10/618,481, filed on Jul. 11, 2003, now Pat. No. 7,696,306.

(51) Int. Cl.
*A61K 38/00* (2006.01)
(52) U.S. Cl. ...................................................... 530/300
(58) Field of Classification Search .................. None
See application file for complete search history.

(56) References Cited

U.S. PATENT DOCUMENTS

| | | | |
|---|---|---|---|
| 4,963,484 | A | 10/1990 | Kufe |
| 5,744,144 | A | 4/1998 | Finn et al. |
| 5,827,666 | A | 10/1998 | Finn et al. |
| 6,344,203 | B1 | 2/2002 | Sandrin et al. |
| 6,548,643 | B1 | 4/2003 | McKenzie et al. |

FOREIGN PATENT DOCUMENTS

| | | |
|---|---|---|
| WO | 88/05054 | 7/1988 |
| WO | 00/25827 | 5/2000 |
| WO | WO 0118035 A2 * | 3/2001 |
| WO | 01/57068 | 8/2001 |
| WO | 02/058450 | 8/2002 |

OTHER PUBLICATIONS

Brossart, P., et al. "Induction of cytotoxic T-lymphocyte responses in vivo after vaccinations with peptide-pulsed dendritic cells." Blood. Nov. 1, 2000;96(9):3102-8.
Brossart, P., et al. "Identification of HLA-A2-restricted T-cell epitopes derived from the MUC1 tumor antigen for broadly applicable vaccine therapies." Blood. Jun. 15, 1999;93(12):4309-17.
Chen, C.H., et al. "Experimental vaccine strategies for cancer immunotherapy." J Biomed Sci. Jul.-Aug. 1998;5(4):231-52.
Croce, M.V., et al. "Expression of tumour associated antigens in normal, benign and malignant human mammary epithelial tissue: a comparative immunohistochemical study." Anticancer Res. Nov.-Dec. 1997;17(6D):4287-92.
Finn, O.J., et al. "MUC-1 epithelial tumor mucin-based immunity and cancer vaccines." Immunol Rev. Jun. 1995;145:61-89.
Graham, R.A., et al. "The polymorphic epithelial mucin: potential as an immunogen for a cancer vaccine." Cancer Immunol Immunother. Feb. 1996;42(2):71-80.
Graham, R.A., et al. "Intramuscular immunisation with MUC1 cDNA can protect C57 mice challenged with MUC1-expressing syngeneic mouse tumour cells." Int J Cancer. Mar. 1, 1996;65(5):664-70.
Heukamp, L.C., et al. "Identification of three non-VNTR MUC1-derived HLA-A*0201-restricted T-cell epitopes that induce protective anti-tumor immunity in HLA-A2/K(b)-transgenic mice." Int J Cancer. Feb. 1, 2001;91(3):385-92.
Heukamp, L.C., et al. "Effective immunotherapy of cancer in MUC1-transgenic mice using clonal cytotoxic T lymphocytes directed against an immunodominant MUC1 epitope." J Immunother. Jan.-Feb. 2002;25(1):46-56.
Morikane, K., et al. "Organ-specific pancreatic tumor growth properties and tumor immunity." Cancer Immunol Immunother. Jan. 1999;47(5):287-96.
Morikane, K., et al. "Influence of organ site and tumor cell type on MUC1-specific tumor immunity." Int Immunol. Feb. 2001;13(2):233-40.
Reddish, M., et al. "Anti-MUC1 class I restricted CTLs in metastatic breast cancer patients immunized with a synthetic MUC1 peptide." Int J Cancer. Jun. 10, 1998;76(6):817-23.
Rowse, G.J., et al. "Tolerance and immunity to MUC1 in a human MUC1 transgenic murine model." Cancer Res. Jan. 15, 1998;58(2):315-21.
Sivinski, C.L., et al. "Molecular requirements for CD8-mediated rejection of a MUC1-expressing pancreatic carcinoma: implications for tumor vaccines." Cancer Immunol Immunother. Aug. 2002;51(6):327-40. Epub May 4, 2002.
Tempero, R.M., et al. "CD4+ lymphocytes provide MUC1-specific tumor immunity in vivo that is undetectable in vitro and is absent in MUC1 transgenic mice." J Immunol. Nov. 15, 1998;161(10):5500-6.
Tempero, R.M., et al. "Passively transferred anti-MUC1 antibodies cause neither autoimmune disorders nor immunity against transplanted tumors in MUC1 transgenic mice." Int J Cancer. Feb. 9, 1999;80(4):595-9.
Vanlith, M.L., et al. "MUC1-specific anti-tumor responses: molecular requirements for CD4-mediated responses." Int Immunol. Aug. 2002;14(8):873-82.
Hoover, H.C., et al. "Adjuvant active specific immunotherapy for human colorectal cancer: 6.5-year median follow-up of a phase III prospectively randomized trial." J Clin Oncol. Mar. 1993;11(3):390-9.
Byrd, J.C., et al. "Mucins and mucin binding proteins in colorectal cancer." Cancer Metastasis Rev. Jan.-Jun. 2004;23(1-2):77-99.

\* cited by examiner

*Primary Examiner* — Hong Sang
(74) *Attorney, Agent, or Firm* — Dann Dorfmann Herrell & Skillman; Robert C. Netter, Jr.

(57) ABSTRACT

The present invention relates to a MUC1 cytoplasmic tail peptide or portion thereof. These peptides are useful for inducing an immune response to MUC1-expressing tumor cells and thus for preventing or treating cancer.

7 Claims, No Drawings

COMPOSITIONS AND METHODS FOR PREVENTING OR TREATING CANCER

The present application is a divisional application of U.S. patent application Ser. No. 10/618,481, filed on Jul. 11, 2003, now U.S. Pat. No. 7,696,306. The entire disclosure of the foregoing application is incorporated by reference herein.

INTRODUCTION

This invention was made with government support under grant Nos. CA72712, CA57362, and CA09476 awarded by the National Institutes of Health. The government has certain rights in this invention.

BACKGROUND OF THE INVENTION

MUC1 is a large, transmembrane glycoprotein expressed on the apical surface of many types of polarized epithelia including pancreas, lung, breast and the gastrointestinal tract (Finn, et al. (1995) *Immunol. Rev.* 145:61). MUC1 is overexpressed and differentially glycosylated by a number of adenocarcinomas (Croce, et al. (1997) *Anticancer Res.* 17:4287) and has been evaluated as a candidate antigen for active immunotherapy protocols. Humoral and cell-mediated immune responses against MUC1 are detected in patients with MUC1+ tumors, as measured in vitro (Domenech, et al. (1995) *J. Immunol.* 155:4766; Petrarca, et al. (1999) *Cancer Immunol. Immunother.* 47:272; Nakamura, et al. (1998) *J. Gastroenterol.* 33:354); however, these responses are ineffective at eliminating the tumors in vivo.

A number of MUC1-based immunogens have been evaluated as potential cancer vaccines (Graham, et al. (1996) *Int. J. Cancer* 65:664; Chien-Hung and Wu (1998) *J. Biomed. Sci.* 5:231; Reddish, et al. (1998) *Int. J. Cancer* 76:817; Heukamp, et al. (2002) *J. Immunother.* 25:46). These include whole cells expressing MUC1, MUC1 purified from tumor cells, and peptide or glycopeptide fragments derived from the tandem repeat region of MUC1 (Finn, et al. (1995) supra; Graham, et al. (1996) *Cancer Immunol. Immunother.* 42:71; U.S. Pat. Nos. 5,744,144, 5,827,666 WO 88/05054, U.S. Pat. Nos. 4,963,484 and 6,344,203). Clinical trials that utilized MUC1 as a vaccine component focused on the tandem repeat region (Finn, et al. (1995) supra; Graham, et al. (1996) supra; Chien-Hung and Wu (1998) supra; Reddish, et al. (1998) supra). Putative epitopes from regions outside of the tandem repeat region of MUC1 have also been investigated (Brossart, et al. (2000) *Blood* 96:3102; Brossart, et al. (1999) *Blood* 93:4309; Heukamp, et al. (2001) *Int. J. Cancer* 91:385); however, other potentially important epitopes from this tumor-associated antigen, especially those in the cytoplasmic tail, have not been studied. Most studies have used in vitro assays to investigate that the tandem repeat region contains immunodominant epitopes for production of MUC1 specific antibodies and cytotoxic T-lymphocytes (CTL). However, it has been shown that in vitro assays of cytolytic responses do not accurately predict MUC1-specific tumor rejection (Tempero, et al. (1998) *J. Immunol.* 161:5500). For example, no detectable differences were observed in the anti-MUC1 CTL precursor frequencies of wild-type C57BL/6 mice and C57BL/6 mice transgenic for human MUC1 (MUC1.Tg) (Tempero, et al. (1998) supra), although wild-type mice rejected MUC1-expressing tumors in a MUC1-specific manner while MUC1.Tg mice did not reject these tumors and showed evidence of immunological tolerance to MUC1 (Tempero, et al. (1998) supra; Rowse, et al. (1998) *Cancer Res.* 58:315).

In vivo immune responses directed against tumor-associated MUC1 have also been analyzed. The nature of cellular immune responses that mediate rejection of MUC1-expressing tumors in mice was investigated by experiments that depleted CD4+, CD8+ or both T cell subsets in vivo. CD4+ cells were required for elimination of a human MUC1-expressing murine melanoma cell line (B16.MUC1), and CD8+ cells were required for the elimination of a human MUC1-expressing murine pancreatic carcinoma cell line (Panc02.MUC1), in wild-type C57BL/6 mice (Tempero, et al. (1999) *Int. J. Cancer* 80:595; Morikane, et al. (2001) *Int. Immunol.* 13:233). Studies using mice deficient in molecular components critical to the immune responses (VanLith, et al. (2002) *Int. Immunol.* 14:873; Sivinski, et al. (2002) *Cancer Immunol. Immunother.* 51:327) further showed that both CD4+ and CD8+ responses were mediated by α/βT cell receptors and required costimulation through CD28, as well as interactions between CD40 and CD40 ligand, and the activities of interferon γ (IFNγ), and lymphotoxin α. A number of other factors (IL4, IL10, IL12, TNFR-1) were not required. There were differences in the effector mechanisms as the CD8-mediated cytotoxicity required perforin but not FasL; in contrast, the CD4-mediated cytotoxic response required both perforin and FasL.

SUMMARY OF THE INVENTION

One aspect of the present invention is a MUC1 cytoplasmic tail peptide of SEQ ID NO:1 or a portion thereof for preventing or treating cancer in a subject. In a preferred embodiment, the MUC1 cytoplasmic tail peptide of SEQ ID NO:1 is part of a vaccine.

Another aspect of the present invention is a method for preventing or treating cancer in a subject. The method involves administering to a subject an effective amount of a MUC1 cytoplasmic tail peptide of SEQ ID NO:1 or portion thereof so that cancer is prevented or treated in the subject.

DETAILED DESCRIPTION OF THE INVENTION

Epitopes of MUC1 have now been found that are recognized and required by the different MUC1 specific T cell populations (CD4 and CD8) mediating the antitumor responses. Putative epitopes were mapped by challenging mice with tumor cell lines (B16 and Panc02) that expressed constructs of human MUC1 in which portions of the coding sequences for the protein were deleted. The C-terminus of the cytoplasmic tail (CT) and the tandem repeat (TR) portion of MUC1 were required for rejection of B16.MUC1, while rejection of Panc02.MUC1 required a distinct portion of the cytoplasmic tail of MUC1, and not the tandem repeat. Vaccination with peptides derived from the amino acid sequence of MUC1 cytoplasmic tail generated protective immune responses against MUC1-expressing tumors in MUC1.Tg mice. Survival of MUC1.Tg mice challenged with MUC1-expressing B16 or Panc02 tumor cells was significantly prolonged following vaccination with three overlapping peptides spanning the entire cytoplasmic tail portion of MUC1. Further, vaccination with MUC1 cytoplasmic tail peptides did not induce detectable autoimmune responses. These results demonstrate the importance of immunogenic epitopes outside of the tandem repeat of MUC1 and indicate that immunization with MUC1 cytoplasmic tail peptides is an effective anti-cancer immunotherapeutic approach.

Initially, the surface expression of human MUC1 variants encoded by deletion constructs expressed in B16 and Panc02 cells was evaluated by flow cytometry. Control transfected B16 (B16.neo) and Panc02 (Panc02.neo) were unreactive with the M2 or anti-MUC1 HMFG-2 antibodies. At least two representative clones of each cell line, with similar in vitro growth rates, and expressing similar levels of the MUC1 isoforms, as determined by western blot analysis, were selected for further studies.

Wild-type C57BL/6 mice produce MUC1-specific immune responses when challenged with MUC1-expressing B16 tumor cells (Tempero, et al. (1998) supra; Rowse, et al. (1998) supra), and Panc02 tumor cells (Morikane, et al. (2001) supra; Morikane, et al. (1999) *Cancer Immunol. Immunother.* 47:287), which are lacking in MUC1.Tg mice because of immunological tolerance, as evidenced in vivo by differences in survival among these strains. It has now been shown that these immune responses in wild-type mice against B16.MUC1 and Panc02.MUC1 are MUC1-specific as the survival of wild-type and MUC1.Tg mice challenged with B16.neo or Panc02.neo cells were statistically indistinguishable (p>0.05). Immunodominant epitopes for MUC1-specific immune responses in vivo were identified by challenging mice with tumors expressing recombinant isoforms of MUC1 that lacked defined regions of the cytoplasmic tail or tandem repeat. Evidence that the deleted portion of MUC1 contributed to MUC1-specific immune responses was obtained when survival curves for wild-type animals challenged with B16 or Panc02 tumor cells expressing the deleted forms were similar to those of MUC1.Tg mice or mice challenged with MUC1-negative controls, B16.neo or Panc02.neo. If the deleted portion of MUC1 was not required for MUC1-specific rejection of tumors, then the survival curves would have more closely resembled those of wild-type mice challenged with B16 or Panc02 cells expressing full-length MUC1.

The contribution of the cytoplasmic tail of MUC1 to MUC1-specific immune responses against MUC1 expressing B16 tumors was analyzed. The cytoplasmic tail was examined for epitopes that contributed to MUC1-specific immune responses directed against B16.MUC1 tumor cells. Wild-type and MUC1.Tg mice were challenged subcutaneously with $2 \times 10^4$ B16 tumor cells expressing a construct in which all but three amino acids of the C-terminus were deleted (B16.MUC1.CT3). The removal of the cytoplasmic tail eliminated MUC1-specific immune responses toward B16.MUC1 (p>0.05), indicating that the cytoplasmic tail was critical to the immunological rejection of these tumors (Table 1).

TABLE 1

| Tumor Cell Type | Difference in Median Survival (Wildtype-MUC1.Tg) | p Value |
| --- | --- | --- |
| B16.MUC1 | 14.00 Days | <0.0001 |
| B16.neo | −1.00 Days | 0.518 |
| B16.MUC1.CT3 | 0.00 Days | 0.322 |
| B16.MUC1.CT33 | 1.00 Days | 0.100 |
| B16.MUC1.CT45 | −1.50 Days | 0.253 |
| B16.MUC1(ΔTR) | 0.00 Days | 0.231 |

P values were determined from Kaplan-Meier survival curves.

Immune responses to two additional constructs expressed by B16 tumor cells were examined. In these constructs the final 36 amino acids (MUC1.CT33) or the final 24 amino acids (MUC1.CT45) of the cytoplasmic tail were deleted. MUC1-specific tumor rejection was not detected in wild-type mice challenged with B16 tumor cells that expressed either MUC1.CT33 (p>0.05) or MUC1.CT45 (p>0.05). These results indicated that the final 24 amino acid segment of the cytoplasmic tail contained an epitope or region that was critical for immunological responses that mediated rejection of MUC1-expressing B16 tumor cells.

The contribution of the tandem repeat to MUC1-specific immune responses directed against B16.MUC1 tumor cells was similarly evaluated. Wild-type and MUC1.Tg mice were challenged subcutaneously with $2 \times 10^4$ B16 cells expressing a construct in which the large, extracellular tandem repeat portion was deleted (B16.MUC1 (ΔTR)). Wild-type mice challenged with B16.MUC1 (ΔTR) experienced survival similar to MUC1.Tg mice challenged with this tumor cell line (p>0.05). These findings indicate that the tandem repeat was an important immunological target during rejection of B16.MUC1 tumor cells, when expressed together with the final 24 amino acid segment of the cytoplasmic tail.

In parallel studies, the contribution of the cytoplasmic tail to MUC1-specific immune responses against MUC1-expressing Panc02 tumor cells was determined. It has been demonstrated that wild-type C57BL/6 mice produce cell-mediated, MUC1-specific immune responses that reject MUC1-expressing Panc02 tumors, whereas MUC1.Tg mice do not reject these tumors (Morikane, et al. (2001) supra; Morikane, et al. (1999) supra). Groups of wild-type and MUC1.Tg mice were challenged subcutaneously with $1 \times 10^6$ Panc02 tumor cells expressing MUC1.CT3. Similar to results using B16.MUC1.CT3 tumor cells, the removal of the cytoplasmic tail eliminated MUC1-specific immune responses toward Panc02.MUC1 (p>0.05) (Table 2).

TABLE 2

| Tumor Cell Type | Difference in Median Survival (Wildtype-MUC1.Tg) | p Value |
| --- | --- | --- |
| Panc02.MUC1 | >34.50 Days | 0.01 |
| Panc02.neo | −4.00 Days | 0.38 |
| Panc02.MUC1.CT3 | 3.00 Days | 0.44 |
| Panc02.MUC1.CT33 | 29.00 Days | 0.0056 |
| Panc02.MUC1.CT45 | 18.00 Days | <0.0001 |
| Panc02.MUC1(ΔTR) | 8.00 Days | 0.0058 |

P values were determined from Kaplan-Meier survival curves.

Further analysis of the cytoplasmic tail to MUC1-specific immune responses against MUC1-expressing Panc02 tumor cells was conducted. The survival of wild-type and MUC1.Tg mice following challenge with $1 \times 10^6$ Panc02 tumor cells expressing MUC1.CT33 was determined. In contrast to results with B16 tumor cells expressing this form of MUC1, wild-type mice rejected these tumors and MUC1.Tg mice did not reject these tumors (p<0.05).

The survival of wild-type and MUC1.Tg mice following challenge with $1 \times 10^6$ Panc02 tumor cells expressing MUC1.CT45 was determined. The wild-type mice rejected MUC1.CT45-expressing tumors in a MUC1-specific manner, whereas MUC1.Tg mice did not (p<0.05). These findings indicated that an epitope or region between amino acid residues three and 33 of the cytoplasmic tail contributed to immunological responses necessary to reject MUC1-expressing Panc02 tumors.

The contribution of the tandem repeat to MUC1-specific immune responses to Panc02.MUC1 was determined. Wild-type and MUC1.Tg mice were challenged with $1 \times 10^6$ Panc02 tumor cells expressing MUC1 (ΔTR). Prolonged survival was observed for wild-type mice compared to MUC1.Tg mice following challenge with Panc02.MUC1 (ΔTR) tumor cells (p<0.05). These results indicated that the tandem repeat portion of MUC1 was not required to reject Panc02.MUC1 tumor cells in a MUC1-specific manner.

Results provided herein demonstrate that epitopes in the MUC1 cytoplasmic tail are critical for the immunological rejection of two distinct MUC1-expressing tumors. Accordingly, the MUC1 cytoplasmic tail amino acid sequence was analyzed using two independent web-based algorithms that predict potential binding to major histocompatibility complex (MHC) class I- and MHC class II molecules. Epitope prediction was conducted for the 72 amino acid residue sequence of MUC1 cytoplasmic tail: Cys-Gln-Cys-Arg-Arg-Lys-Asn-Tyr-Gly-Gln-Leu-Asp-Ile-Phe-Pro-Ala-Arg-Asp-Thr-Tyr-His-Pro-Met-Ser-Glu-Tyr-Pro-Thr-Tyr-His-Thr-His-Gly-Arg-Tyr-Val-Pro-Pro-Ser-Ser-Thr-Asp-Arg-Ser-Pro-Tyr-Glu-Lys-Val-Ser-Ala-Gly-Asn-Gly-Gly-Ser-Ser-Leu-Ser-Tyr-Thr-Asn-Pro-Ala-Val-Ala-Ala-Ala-Ser-Ala-Asn-Leu (SEQ ID NO:1). Multiple peptides within the regions required for rejection of Panc02.MUC1 (amino acids 3-33) and B16.MUC1 (amino acids 45-69) were predicted to exhibit high binding affinity for murine MHC class I. The results for binding to $K^b$ and $D^b$ are summarized in Table 3.

TABLE 3

| Predicted Epitope | Location | H-2 Molecule | SYFPEITHI Score[1] | BIMAS Score[2] |
|---|---|---|---|---|
| Cys-Arg-Arg-Lys-Asn-Tyr-Gly-Gln-Leu (SEQ ID NO: 2) | 3 | H2-$D^b$ | 20 | 10.171 |
| Val-Ser-Ala-Gly-Asn-Gly-Gly-Ser-Ser (SEQ ID NO: 3) | 49 | H2-$D^b$ | 14 | No Score Obtained |
| Leu-Ser-Tyr-Thr-Asn-Pro-Ala-Val-Ala (SEQ ID NO: 4) | 58 | H2-$D^b$ | 13 | 33.480 |
| Ser-Ala-Gly-Asn-Gly-Gly-Ser-Ser-Leu (SEQ ID NO: 5) | 50 | H2-$D^b$ | 18 | 22.176 |
| Ala-Val-Ala-Ala-Ala-Ser-Ala-Asn-Leu (SEQ ID NO: 6) | 64 | H2-$D^b$ | 12 | 10.088 |
| Val-Ser-Ala-Gly-Asn-Gly-Gly-Ser-Ser-Leu (SEQ ID NO: 7) | 49 | H2-$D^b$ | 25 | Decamer Option N/A |
| Pro-Ala-Val-Ala-Ala-Ala-Ser-Ala-Asn-Leu (SEQ ID NO: 8) | 63 | H2-$D^b$ | 15 | Decamer Option N/A |
| Leu-Ser-Tyr-Thr-Asn-Pro-Ala-Val-Ala-Ala (SEQ ID NO: 9) | 58 | H2-$D^b$ | 14 | Decamer Option N/A |
| Phe-Pro-Ala-Arg-Asp-Thr-Tyr-His-Pro-Met (SEQ ID NO: 10) | 14 | H2-$D^b$ | 13 | Decamer Option N/A |
| Arg-Arg-Lys-Asn-Tyr-Gly-Gln-Leu (SEQ ID NO: 11) | 4 | H2-$K^b$ | 22 | Octamer Option N/A |
| Asp-Arg-Ser-Pro-Tyr-Glu-Lys-Val (SEQ ID NO: 12) | 42 | H2-$K^b$ | 18 | Octamer Option N/A |
| Ala-Arg-Asp-Thr-Tyr-His-Pro-Met (SEQ ID NO: 13) | 16 | H2-$K^b$ | 17 | Octamer Option N/A |
| Ser-Ser-Leu-Ser-Tyr-Thr-Asn-Pro (SEQ ID NO: 14) | 56 | H2-$K^b$ | 14 | Octamer Option N/A |
| Cys-Arg-Arg-Lys-Asn-Tyr-Gly-Gln-Leu (SEQ ID NO: 15) | 3 | H2-$K^b$ | No Score Obtained | 1.440 |
| Ala-Val-Ala-Ala-Ala-Ser-Ala-Asn-Leu (SEQ ID NO: 6) | 64 | H2-$K^b$ | No Score Obtained | 1.210 |
| Ser-Ala-Gly-Asn-Gly-Gly-Ser-Ser-Leu (SEQ ID NO: 5) | 50 | H2-$K^b$ | No Score Obtained | 1.100 |
| Ser-Glu-Tyr-Pro-Thr-Tyr-His-Thr-His (SEQ ID NO: 16) | 24 | H2-$K^b$ | No Score Obtained | 1.100 |

Location is the position of the first residue. [1]Score obtained using program developed by Rammensee, et al. (1999) Immunogenetics 50: 213. [2]Score obtained using program developed by Parker, et al. (1994) J. Immunol. 152: 163. Score for H2-$D^b$ obtained using $D^b$ revised. N/A is not available.

Similar analysis revealed numerous putative epitopes within these regions predicted to bind human HLA molecules (Table 4).

TABLE 4

| Predicted Epitope | Location | HLA Molecule | SYFPEITHI Score[1,3] | BIMAS Score[2,3] |
|---|---|---|---|---|
| Ser-Leu-Ser-Tyr-Thr-Asn-Pro-Ala-Val (SEQ ID NO: 17) | 57 | HLA-A*0201 | 23 | 69.552 |
| Ser-Ala-Gly-Asn-Gly-Gly-Ser-Ser-Leu (SEQ ID NO: 5) | 50 | HLA-A*0201 | 20 | 0.297 |
| Tyr-Thr-Asn-Pro-Ala-Val-Ala-Ala-Ala (SEQ ID NO: 18) | 60 | HLA-A*0201 | 20 | 0.730 |
| Ala-Val-Ala-Ala-Ala-Ser-Ala-Asn-Leu (SEQ ID NO: 6) | 64 | HLA-A*0201 | 20 | 1.869 |
| Ser-Tyr-Thr-Asn-Pro-Ala-Val-Ala-Ala-Ala (SEQ ID NO: 19) | 59 | HLA-A*0203 | 27 | HLA Type N/A |
| Asp-Thr-Tyr-His-Pro-Met-Ser-Glu-Tyr (SEQ ID NO: 20) | 18 | HLA-A1 | 22 | 1.250 |

TABLE 4-continued

| Predicted Epitope | HLA Location | Molecule | SYFPEITHI Score[1,3] | BIMAS Score[2,3] |
|---|---|---|---|---|
| Gly-Asn-Gly-Gly-Ser-Ser-Leu-Ser-Tyr (SEQ ID NO: 21) | 52 | HLA-A1 | 22 | 0.625 |
| Pro-Thr-Tyr-His-Thr-His-Gly-Arg-Tyr (SEQ ID NO: 22) | 27 | HLA-A1 | 21 | 0.125 |
| Asp-Ile-Phe-Pro-Ala-Arg-Asp-Thr-Tyr (SEQ ID NO: 23) | 12 | HLA-A1 | 20 | 5.000 |
| Pro-Ser-Ser-Thr-Asp-Arg-Ser-Pro-Tyr (SEQ ID NO: 24) | 38 | HLA-A1 | 20 | 0.075 |
| Ala-Gly-Asn-Gly-Gly-Ser-Ser-Leu-Ser-Tyr (SEQ ID NO: 25) | 51 | HLA-A1 | 23 | No Score Obtained |
| Ser-Thr-Asp-Arg-Ser-Pro-Tyr-Glu-Lys-Val (SEQ ID NO: 26) | 40 | HLA-A1 | 20 | No Score Obtained |
| Asp-Thr-Tyr-His-Pro-Met-Ser-Glu-Tyr (SEQ ID NO: 20) | 18 | HLA-A26 | 32 | HLA Type N/A |
| Asp-Ile-Phe-Pro-Ala-Arg-Asp-Thr-Tyr (SEQ ID NO: 23) | 12 | HLA-A26 | 30 | HLA Type N/A |
| Asp-Ile-Phe-Pro-Ala-Arg-Asp-Thr-Tyr-His (SEQ ID NO: 27) | 12 | HLA-A26 | 20 | HLA Type N/A |
| Asp-Ile-Phe-Pro-Ala-Arg-Asp-Thr-Tyr (SEQ ID NO: 23) | 12 | HLA-A3 | 22 | 0.900 |
| Lys-Val-Ser-Ala-Gly-Asn-Gly-Gly-Ser-Ser (SEQ ID NO: 28) | 48 | HLA-A3 | 21 | No Score Obtained |
| Tyr-Val-Pro-Pro-Ser-Ser-Thr-Asp-Arg (SEQ ID NO: 29) | 35 | HLA-A68.1 | HLA Type N/A | 300.000 |
| Arg-Arg-Lys-Asn-Tyr-Gly-Gln-Leu (SEQ ID NO: 11) | 4 | HLA-B*08 | 20 | HLA Type N/A |
| Ser-Pro-Tyr-Glu-Lys-Val-Ser-Ala (SEQ ID NO: 30) | 44 | HLA-B*08 | 20 | HLA Type N/A |
| Ser-Pro-Tyr-Glu-Lys-Val-Ser-Ala-Gly (SEQ ID NO: 31) | 44 | HLA-B*08 | 22 | HLA Type N/A |
| Cys-Arg-Arg-Lys-Asn-Tyr-Gly-Gln-Leu (SEQ ID NO: 15) | 3 | HLA-B*2705 | 23 | HLA Type N/A |
| Gly-Arg-Tyr-Val-Pro-Pro-Ser-Ser-Thr (SEQ ID NO: 32) | 30 | HLA-B*2705 | 18 | 100.000 |
| Ala-Arg-Asp-Thr-Tyr-His-Pro-Met-Ser (SEQ ID NO: 33) | 13 | HLA-B*2705 | 12 | 200.000 |
| Lys-Asn-Tyr-Gly-Gln-Leu-Asp-Ile-Phe (SEQ ID NO: 34) | 6 | HLA-B*2705 | 17 | 150.000 |
| Gly-Gln-Leu-Asp-Ile-Phe-Pro-Ala-Arg (SEQ ID NO: 35) | 9 | HLA-B*2705 | 17 | 100.000 |
| Arg-Arg-Lys-Asn-Tyr-Gly-Gln-Leu-Asp (SEQ ID NO: 36) | 4 | HLA-B*2705 | 14 | 60.000 |
| Cys-Arg-Arg-Lys-Asn-Tyr-Gly-Gln-Leu (SEQ ID NO: 15) | 3 | HLA-B*2709 | 21 | HLA Type N/A |
| His-Pro-Met-Ser-Glu-Tyr-Pro-Thr-Tyr (SEQ ID NO: 37) | 21 | HLA-B*3501 | HLA Type N/A | 60.000 |
| Ser-Ala-Gly-Asn-Gly-Gly-Ser-Ser-Leu (SEQ ID NO: 5) | 50 | HLA-B*5102 | HLA Type N/A | 60.500 |
| Arg-Lys-Asn-Tyr-Gly-Gln-Leu-Asp-Ile-Phe-Pro-Ala-Arg-Asp-Thr (SEQ ID NO: 38) | 5 | HLA-DRB1*0101 | 26 | HLA Type N/A |
| Arg-Ser-Pro-Tyr-Glu-Lys-Val-Ser-Ala-Gly-Asn-Gly-Gly-Ser-Ser (SEQ ID NO: 39) | 43 | HLA-DRB1*0101 | 26 | HLA Type N/A |
| Leu-Asp-Ile-Phe-Pro-Ala-Arg-Asp-Thr-Tyr-His-Pro-Met-Ser-Glu (SEQ ID NO: 40) | 11 | HLA-DRB1*0101 | 24 | HLA Type N/A |
| Tyr-Glu-Lys-Val-Ser-Ala-Gly-Asn-Gly-Gly-Ser-Ser-Leu-Ser-Tyr (SEQ ID NO: 41) | 46 | HLA-DRB1*0101 | 24 | HLA Type N/A |
| Gly-Arg-Tyr-Val-Pro-Pro-Ser-Ser-Thr-Asp-Arg-Ser-Pro-Tyr-Glu (SEQ ID NO: 42) | 33 | HLA-DRB1*0101 | 22 | HLA Type N/A |

TABLE 4-continued

| Predicted Epitope | Location | HLA Molecule | SYFPEITHI Score[1,3] | BIMAS Score[2,3] |
|---|---|---|---|---|
| Gly-Ser-Ser-Leu-Ser-Tyr-Thr-Asn-Pro-Ala-Val-Ala-Ala-Ala-Ser (SEQ ID NO: 43) | 55 | HLA-DRB1*0101 | 22 | HLA Type N/A |
| Tyr-Gly-Gln-Leu-Asp-Ile-Phe-Pro-Ala-Arg-Asp-Thr-Tyr-His-Pro (SEQ ID NO: 44) | 8 | HLA-DRB1*0101 | 20 | HLA Type N/A |
| Arg-Lys-Asn-Tyr-Gly-Gln-Leu-Asp-Ile-Phe-Pro-Ala-Arg-Asp-Thr (SEQ ID NO: 38) | 5 | HLA-DRB1*0401 | 22 | HLA Type N/A |
| Tyr-Gly-Gln-Leu-Asp-Ile-Phe-Pro-Ala-Arg-Asp-Thr-Tyr-His-Pro (SEQ ID NO: 44) | 8 | HLA-DRB1*0401 | 20 | HLA Type N/A |
| Tyr-His-Pro-Met-Ser-Glu-Tyr-Pro-Thr-Tyr-His-Thr-His-Gly-Arg (SEQ ID NO: 45) | 20 | HLA-DRB1*0401 | 20 | HLA Type N/A |
| Gly-Arg-Tyr-Val-Pro-Pro-Ser-Ser-Thr-Asp-Arg-Ser-Pro-Tyr-Glu (SEQ ID NO: 42) | 33 | HLA-DRB1*0401 | 20 | HLA Type N/A |
| Tyr-Pro-Thr-Tyr-His-Thr-His-Gly-Arg-Tyr-Val-Pro-Pro-Ser-Ser (SEQ ID NO: 46) | 26 | HLA-DRB1*1101 | 25 | HLA Type N/A |
| Arg-Lys-Asn-Tyr-Gly-Gln-Leu-Asp-Ile-Phe-Pro-Ala-Arg-Asp-Thr (SEQ ID NO: 38) | 5 | HLA-DRB1*1101 | 22 | HLA Type N/A |
| Arg-Ser-Pro-Tyr-Glu-Lys-Val-Ser-Ala-Gly-Asn-Gly-Gly-Ser-Ser (SEQ ID NO: 39) | 43 | HLA-DRB1*1101 | 22 | HLA Type N/A |

Location is the position of the first residue. [1]Score obtained using program developed by Rammensee, et al. (1999) supra. [2]Score obtained using program developed by Parker, et al. (1994) supra. [3]Minimum scores of 20 on the SYFPEITHI site or 60 on the BIMAS site were used. If a score met the requirement of one site, the score of the other site is listed even if the minimum score for that site was not achieved. N/A is not available.

These results demonstrate that the cytoplasmic tail of MUC1, which is 87% identical between humans and mice, may be utilized for methods of immunizing against MUC1-positive tumors in humans.

Accordingly, the efficacy of cytoplasmic tail peptide vaccination was evaluated by challenging MUC1.Tg mice with a lethal dose of MUC1-expressing B16 tumor cells 10 days following vaccination. MUC1.Tg mice vaccinated with MUC1 cytoplasmic tail peptides demonstrated a significant increase in survival compared to MUC1.Tg mice vaccinated with control peptide or nonvaccinated mice ($p<0.05$). Organs expressing endogenous MUC1 were examined at necropsy and histologically to determine whether the vaccination also elicited detectable autoimmunity. No evidence of autoimmunity was detected in any of the animals.

MUC1 expression in tumors was measured among vaccinated, control peptide-vaccinated and nonvaccinated mice. Serial sections of tumor tissue were examined for expression of MUC1 by immunohistochemistry. Tumors from control peptide-vaccinated MUC1.Tg mice challenged with B16.MUC1 showed significantly greater expression of MUC1 than vaccinated mice challenged with B16.MUC1. Similar results were observed in tumors obtained from nonvaccinated mice challenged with B16.MUC1 compared to vaccinated mice challenged with B16.MUC1.

The efficacy of MUC1 cytoplasmic tail peptide vaccinations to protect against MUC1-expressing Panc02 tumors was evaluated by challenging MUC1.Tg mice with a lethal dose of Panc02.MUC1 tumor cells 10 days following the final vaccination. MUC1.Tg mice vaccinated with MUC1 cytoplasmic tail peptide Cys-Gln-Cys-Arg-Arg-Lys-Asn-Tyr-Gly-Gln-Leu-Asp-Ile-Phe-Pro-Ala-Arg-Asp-Thr-Tyr-His-Pro-Met-Ser-Glu-Tyr-Pro-Thr-Tyr-His (SEQ ID NO:47) demonstrated a significant increase in survival compared to MUC1.Tg mice vaccinated with control peptide or nonvaccinated mice ($p<0.05$). Organs from these mice examined at necropsy and histologically showed no evidence of autoimmunity.

Serial sections of tumor tissue derived from vaccinated, control peptide-vaccinated, and nonvaccinated mice were evaluated by immunohistochemistry for expression of MUC1. Tumors from control peptide-vaccinated MUC1.Tg mice challenged with Panc02.MUC1 showed significantly more MUC1 expression than vaccinated mice challenged with Panc02.MUC1. Similar reactivity was observed in tumors obtained from nonvaccinated mice challenged with Panc02.MUC1 compared to vaccinated mice challenged with Panc02.MUC1. These results, combined with survival data, indicated that MUC1-expressing tumor cells were eliminated, and that tumor growth was primarily due to MUC1-negative variants. Moreover, the observed anti-MUC1 immune responses were tumor specific, as there was no evidence of autoimmune reactions.

To investigate whether observed anti-MUC1 immune responses were mediated by humoral and/or cell-mediated mechanisms, ELISA and CTL assays were performed. For ELISA, sera from vaccinated, control peptide-vaccinated, and nonvaccinated mice challenged with MUC1-expressing B16 or Panc02 tumors were tested for production of antibodies to a peptide of SEQ ID NO:47, peptide His-Pro-Met-Ser-Glu-Tyr-Pro-Thr-Tyr-His-Thr-His-Gly-Arg-Tyr-Val-Pro-Pro-Ser-Ser-Thr-Asp-Arg-Ser-Pro-Tyr-Glu-Lys-Val-Ser-Ala-Gly (SEQ ID NO:48), peptide Ser-Thr-Asp-Arg-Ser-Pro-Tyr-Glu-Lys-Val-Ser-Ala-Gly-Asn-Gly-Gly-Ser-Ser-Leu-Ser-Tyr-Thr-Asn-Pro-Ala-Val-Ala-Ala-Ala-Ser-Ala-Asn-Leu (SEQ ID NO:49), control peptide, or tandem repeat peptide. There were no statistically significant differences in antibody responses to peptides among the vaccinated, control peptide-vaccinated and nonvaccinated mice ($p>0.05$) with one exception. Following challenge with MUC1-expressing Panc02 tumor cells, nonvaccinated mice produced significantly more peptide-specific antibodies to peptides compared to vaccinated or control peptide-vaccinated mice ($p<0.05$).

To evaluate generation of MUC1-specific CTL, spleens and lymph nodes were harvested from vaccinated, control peptide-vaccinated and nonvaccinated MUC1.Tg mice challenged with MUC1-expressing B16 or Panc02 tumors. MUC1-specific cytolytic activity was measured against EL4 or EL4.MUC1 cells. CTL were restimulated in vitro for 10 days with EL4 or EL4.MUC1 cells prior to analysis. Cytotoxic responses to EL4.MUC1 cells were similarly low among control peptide-vaccinated and nonvaccinated mice challenged with B16.MUC1 or Panc02.MUC1 (p>0.05). In contrast, lymphocytes obtained from vaccinated mice challenged with B16.MUC1 or Panc02.MUC1 demonstrated significant lysis of EL4.MUC1 cells (p<0.05). These responses were specific for MUC1 because there were no differences of EL4 cell lytic activity among vaccinated, control peptide vaccinated and nonvaccinated mice challenged with MUC1-expressing B16 or Panc02 tumor cells (p>0.05).

It has now been demonstrated that portions of the cytoplasmic tail of MUC1 mediate immunological rejection of MUC1-expressing tumor cells. Further, vaccination of immunologically tolerant MUC1.Tg mice with peptides derived from the amino acid sequence of the MUC1 cytoplasmic tail elicits a protective immune response that significantly prolongs survival of these mice following challenge with MUC1-expressing B16 or Panc02 tumor cells.

Accordingly, one aspect of the present invention is a peptide of at least a portion of a MUC1 cytoplasmic tail peptide of SEQ ID NO:1, wherein said peptide is useful for preventing or treating cancer. A MUC1 cytoplasmic tail peptide which may be used within the scope of the invention includes a full-length MUC1 cytoplasmic tail peptide (SEQ ID NO:1), or a homolog, an allele, an ortholog, or a portion of SEQ ID NO:1 which induces an immune response to MUC1-expressing tumor cells. Preferably, the immune response is characterized by the elicitation of a T cell response (e.g., T helper or cytotoxic T cells) which is brought about by exposure to a MUC1 cytoplasmic tail peptide. More preferably, the MUC1 cytoplasmic tail peptide binds to a MHC class I or MHC class II molecule or is an MHC non-restricted epitope thereby inducing an immune response. In a preferred embodiment of the invention, a portion of a MUC1 cytoplasmic tail peptide encompasses a peptide of SEQ ID NO:47, SEQ ID NO:48 or SEQ ID NO:49. In a more preferred embodiment, a portion of a MUC1 cytoplasmic tail peptide is a 9 to 15 amino acid residue portion of SEQ ID NO:1, e.g., peptides of SEQ ID NO:2 to SEQ ID NO:46.

A MUC1 cytoplasmic tail peptide of the invention may be recombinantly-produced or chemically-synthesized using conventional methods well-known to the skilled artisan.

In general, recombinant production of a MUC1 cytoplasmic tail peptide may require incorporation of nucleic acid sequences encoding said peptide into a recombinant expression vector in a form suitable for expression of the peptide in a host cell. A suitable form for expression provides that the recombinant expression vector includes one or more regulatory sequences operatively-linked to the nucleic acids encoding the a MUC1 cytoplasmic tail peptide in a manner which allows for transcription of the nucleic acids into mRNA and translation of the mRNA into the protein. Regulatory sequences may include promoters, enhancers and other expression control elements (e.g., polyadenylation signals). Such regulatory sequences are known to those skilled in the art and are described in Goeddel D. D., ed., Gene Expression Technology, Academic Press, San Diego, Calif. (1991). It should be understood that the design of the expression vector may depend on such factors as the choice of the host cell to be transfected and/or the level of expression required. Nucleic acid sequences or expression vectors harboring nucleic acid sequences encoding a MUC1 cytoplasmic tail peptide may be introduced into a host cell, which may be of eukaryotic or prokaryotic origin, by standard techniques for transforming cells. Suitable methods for transforming host cells may be found in Sambrook, et al. (Molecular Cloning: A Laboratory Manual, 3rd Edition, Cold Spring Harbor Laboratory Press (2000)) and other laboratory manuals. The number of host cells transformed with a nucleic acid sequence encoding a MUC1 cytoplasmic tail peptide will depend, at least in part, upon the type of recombinant expression vector used and the type of transformation technique used. Nucleic acids may be introduced into a host cell transiently, or more typically, for long-term expression of a MUC1 cytoplasmic tail peptide the nucleic acid sequence is stably integrated into the genome of the host cell or remains as a stable episome in the host cell. Once produced, a MUC1 cytoplasmic tail peptide may be recovered from culture medium as a secreted polypeptide, although it also may be recovered from host cell lysates when directly expressed without a secretory signal. When a MUC1 cytoplasmic tail peptide is expressed in a recombinant cell other than one of human origin, the MUC1 cytoplasmic tail peptide is substantially free of proteins or polypeptides of human origin. However, it may be necessary to purify the MUC1 cytoplasmic tail peptide from recombinant cell proteins or polypeptides using conventional protein purification methods to obtain preparations that are substantially homogeneous as to the MUC1 cytoplasmic tail peptide.

In addition to recombinant production, a MUC1 cytoplasmic tail peptide may be produced by direct peptide synthesis using solid-phase techniques (Merrifield J. (1963) *J. Am. Chem. Soc.* 85:2149-2154). Protein synthesis may be performed using manual techniques or by automation. Automated synthesis may be achieved, for example, using Applied Biosystems 431A Peptide Synthesizer (Perkin Elmer, Boston, Mass.). Various fragments of the MUC1 cytoplasmic tail peptide may be chemically-synthesized separately and combined using chemical methods to produce a full-length molecule.

Whether recombinantly-produced or chemically-synthesized, a MUC1 cytoplasmic tail peptide or portion thereof may be further modified prior to use. For example, the peptides may be glycosylated, phosphorylated or fluorescently-tagged using well-known methods.

MUC1 cytoplasmic tail peptides of the invention are useful in inducing an immune response to MUC1-expressing tumor cells. Accordingly, another aspect of the present invention is a method for preventing or treating cancer in a subject by administering a MUC1 cytoplasmic tail peptide provided herein. Subjects who may benefit from a MUC1 cytoplasmic tail peptide of the invention include those having, at risk of having, or suspected of having cancer. A subject at risk of having cancer may include individuals who have a high probability of developing cancer (e.g., individuals who have been exposed to cancer causing agents) or who may have a genetic predisposition for developing cancer and may benefit from a preventive therapy. Preferably, a subject has, is at risk of having or is suspected of having a cancer in which the tumor cells express MUC1. Cancers which may be prevented or treated include cancers of secretory epithelia origin including, but not limited to, cancers of the pancreas, breast, prostate, liver, colon, and others.

An effective amount of MUC1 cytoplasmic tail peptide which may be used in accordance with the method of the invention is an amount which prevents, eliminates, alleviates, or reduces at least one sign or symptom of a cancer. Signs or symptoms associated with a cancer that may be monitored to determine the effectiveness of a MUC1 cytoplasmic tail peptide include, but are not limited to, tumor size, feelings of weakness, pain perception, and the like. The amount of the MUC1 cytoplasmic tail peptide required to achieve the desired outcome of preventing, eliminating, alleviating or reducing a sign or symptom of cancer will be dependent on the pharmaceutical composition of the MUC1 cytoplasmic tail peptide, the patient and the condition of the patient, the mode of administration, and the type of cancer being prevented or treated. For example, from about 0.05 µg to about 20 mg per kilogram of body weight per day of MUC1 cytoplasmic tail peptide may be administered. Dosage regime may be adjusted to provide the optimum therapeutic response. For example, several divided doses may be administered daily or the dose may be proportionally reduced as indicated by the exigencies of the therapeutic situation. A MUC1 cytoplasmic tail peptide may be administered by continuous or intermittent infusion, parenterally, intramuscularly, subcutaneously, intravenously, intra-arterially, intrathecally; intraarticularly, transdermally, orally, bucally, intranasally, as a suppository or pessary, topically, as an aerosol, spray, or drops, depending upon whether the preparation is used to treat an internal or external cancer. Such administration may be accompanied by pharmacologic studies to determine the optimal dose and schedule and would be within the skill of the ordinary practitioner.

A pharmaceutical composition is one which contains a MUC1 cytoplasmic tail peptide and a pharmaceutically acceptable carrier. A pharmaceutically acceptable carrier is a material useful for the purpose of administering the medicament, which is preferably sterile and non-toxic, and may be solid, liquid, or gaseous materials, which is otherwise inert and medically acceptable, and is compatible with the active ingredients. A generally recognized compendium of methods and ingredients of pharmaceutical compositions is Remington: The Science and Practice of Pharmacy, Alfonso R. Gennaro, editor, 20th ed. Lippincott Williams & Wilkins: Philadelphia, Pa., 2000.

A pharmaceutical composition may contain other active ingredients such as preservatives. A pharmaceutical composition may take the form of a solution, emulsion, suspension, ointment, cream, granule, powder, drops, spray, tablet, capsule, sachet, lozenge, ampoule, pessary, or suppository. Further, a MUC1 cytoplasmic tail peptide may be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

In a preferred embodiment, a MUC1 cytoplasmic tail peptide according to the invention may be administered as a vaccine to cancer patients to induce immunity to MUC1. Accordingly, a MUC1 cytoplasmic tail peptide may be conjugated to a carrier protein such as, for example, tetanus toxoid, diphtheria toxoid or oxidized KLH in order to stimulate T cell help.

It is further contemplated that a MUC1 cytoplasmic tail peptide may be conjugated to other species. The other species comprehended include all chemical species which can be fused to the peptide without affecting the binding of the peptide by T-cells. Specific examples are, for example, other antigens such as epitopes which may elicit a separate immune response, carrier molecules which may aid absorption or protect the peptide from enzyme action in order to improve the effective half-life of the peptide. For example, while it may be desirable to use a peptide of SEQ ID NO:47 or fragment thereof to treat or prevent pancreatic cancer, peptides or fragments of peptides of SEQ ID NO:47 in combination with peptides of the tandem repeat region of MUC1 may be useful in treating or preventing breast cancer.

Compositions and vaccines according to the invention may contain a single MUC1 cytoplasmic tail peptide or a range of MUC1 cytoplasmic tail peptides which cover different or similar epitopes. In addition or alternatively, a single polypeptide may be provided with multiple epitopes. The latter type of vaccine is referred to as a polyvalent vaccine.

The invention is described in greater detail by the following non-limiting examples.

Example 1

Cell Culture

The BL6 variant of the C57BL/6-derived murine melanoma cell line B16 was maintained in Dulbecco's Minimal Essential Medium (DMEM) (GIBCO™ BRL, Div. of Life Technologies Inc., Rockville, Md.) supplemented with 10% heat-inactivated fetal bovine serum (BioWhittaker, Walkersville, Md.), essential amino acids (BioWhittaker), non-essential amino acids (Biowhittaker), sodium pyruvate (Sigma, St. Louis, Mo.), vitamins (GIBCO™), and penicillin/streptomycin (Biowhittaker). Panc02, a methylcholanthrene-induced pancreatic carcinoma syngeneic to C57BL/6, was maintained in McCoy's 5A medium (GIBCO™) supplemented with 10% heat-inactivated fetal bovine serum, and penicillin/streptomycin in a humidified incubator at 37° C. and 5% $CO_2$. EL4 cells were cultured in RPMI 1640 medium (GIBCO™) supplemented with 10% heat-inactivated fetal bovine serum and penicillin/streptomycin in a humidified incubator at 37° C. and 5% $CO_2$. Culture media for MUC1 transfectant clones of B16, Panc02 and EL4 were supplemented with 600 µg/mL G418 (Mediatech, Herndon, Va.).

Example 2

Expression of Epitope-Tagged MUC1 Deletion Constructs

B16 and Panc02 were transfected with plasmid DNA encoding a full-length human MUC1 cDNA (B16.MUC1 or Panc02.MUC1) or control expression vector (B16.neo, or Panc02.neo) as has been described (Rowse, et al. (1998) supra; Morikane, et al. (1999) supra). The full-length cytoplasmic tail was 69 amino acids in length. MUC1 cytoplasmic tail deletion constructs were generated using well-established methods (Pemberton, et al. (1996) *J. Biol. Chem.* 271:2332; Burdick, et al. (1997) *J. Biol. Chem.* 272:24198). The tandem repeat was comprised of a 20 amino acid sequence (Pro-Asp-Thr-Arg-Pro-Ala-Pro-Gly-Ser-Thr-Ala-Pro-Pro-Ala-His-Gly-Val-Thr-Ser-Ala; SEQ ID NO:50) that repeated 42 times. The MUC1 tandem repeat deleted (ATR) construct was generated using well-known methods (Pemberton, et al. (1996) supra; Burdick, et al. (1997) supra). FLAG® epitope-tagged human MUC1 cDNA constructs in which portions of the cytoplasmic tail (MUC1.CT3, MUC1.CT33, MUC1.CT45), or tandem repeat (MUC1 (ΔTR)) of MUC1 were deleted were subcloned into the expression vector pHβ-Apr1-neo using well-known methods (Pemberton, et al. (1996) supra; Burdick, et al. (1997) supra; Gunning, et al. (1987) *Proc. Natl. Acad. Sci. U.S.A.* 84:4831). B16 and Panc02 were transfected with plasmid DNA using the LIPOFECTIN® method (GIBCO™) or the GENEPORTER™ 2 method (Gene Therapy Systems, San Diego, Calif.). Cells were plated in 100 mm tissue culture dishes (Falcon Plastics, BD Labware, Franklin Lakes, N.J.) and grown to approximately 70% confluence. For the LIPOFECTIN® method, growth medium was removed, and the cells were washed with 1× PBS, and incubated 12 hours in 5 mL of serum-free DMEM with 10 μL LIPOFECTIN® reagent and 10 μg plasmid DNA linearized by ScaI digestion. After 48 hours, the transfection medium was replaced with selection medium containing 600 μg/mL G418. For the GENEPORTER™ 2 method, growth medium was removed, and the cells were washed with 1× PBS, and then incubated 48 hours in 5 mL of serum-free DMEM containing 42 μL GENEPORTER™ 2 reagent, 12 μg linearized plasmid DNA linearized by ScaI digestion, and 300 μL DNA diluent B (Gene Therapy Systems). Transfection reactions of Panc02 cells using GENEPORTER™ 2 also contained 50 μL transfection booster 3 (Gene Therapy Systems). After 48 hours, the transfection medium was replaced with selection medium containing 600 μg/mL G418. After approximately 7-10 days, single colonies were selected with cloning cylinders and expanded. Clonal cell lines were evaluated for co-expression of FLAG® epitope and MUC1 epitopes by western blotting with anti-FLAG® antibody (M2) (Sigma) and anti-MUC1 antibodies HMFG-2 or CT-2. Cell lines found to express the FLAG® epitope and MUC1 epitopes by western blotting, were evaluated for FLAG® epitope and MUC1 epitope surface expression by flow cytometry analysis.

Example 3

Preparation of Cell Lysates

Cell lysates were prepared by scraping cells into 1 mL of lysis buffer (10 mM Tris, 150 mM NaCl, 1 mM phenylmethylsulfonyl fluoride, 1% TRITON® X-100) with a rubber cell scraper. Lysates were incubated on ice, for 30 minutes and centrifuged at 4° C. for two minutes at 6,000 rpm to remove cell debris. Supernatants were transferred to fresh tubes and protein content was determined using the BIO-RAD® protein assay (BIO-RAD®, Hercules, Calif.) with bovine serum albumin standards. Cell lysates were stored at −20° C.

Example 4

Immunoblotting

Cell lysates were resolved on 10% denaturing polyacrylamide gels (with 3% polyacrylamide stacking gel), electrophoretically transferred to polyvinylpyrrolidine difluoride membranes, and blocked overnight in blotto (5% dry milk in 1× Tris-buffered saline (0.9% NaCl, 10 mM Tris, pH 7.4, 0.5% $MgCl_2$)). Primary antibodies were diluted 1:2000 in blotto. Incubations were for 1 hour at room temperature with light shaking, followed by three 10 minute washes with blotto. Alkaline phosphatase-conjugated goat anti-mouse secondary antibodies were diluted 1:2500 in blotto, and incubations were for 1 hour at room temperature with light shaking. Following incubation with secondary antibody, the membranes were washed three times as above. Enhanced chemifluorescence (ECF) reagents were applied as per manufacturer instructions (AMERSHAM™ Life Science LTD., Buckinghamshire, UK), and blots were visualized using a Fujifilm LAS-1000 CCD imaging system (Fuji Film Co., Tokyo, JP). Analysis was performed using IR-LAS-1000 Lite V.1.1 software (Fuji).

Example 5

Flow Cytometry

Flow cytometric analysis of MUC1 surface expression on B16 and Panc02 transfectants was performed as follows. Adherent cells were released from tissue culture flasks by treating with 0.05 mM trypsin and 1.5 mM EDTA in phosphate-buffered saline (PBS) for 5 minutes at 37° C. All subsequent steps were carried out on ice. The cells were resuspended in FACS medium (1× PBS, 0.2% BSA, 0.1% sodium azide) at a concentration of $1 \times 10^6$ cells/mL, and incubated with M2 antibody or anti-MUC1 tandem repeat antibody (HMFG-2) for 20 minutes at 4° C. The cells were washed with FACS medium and incubated with a phycoerythrin-conjugated (PE) rabbit anti-mouse secondary antibody (Jackson ImmunoResearch Laboratories, Inc., West Grove, Pa.) for 30 minutes at 4° C. The cells were washed again and resuspended in FACS medium, followed by analysis on a FACS-CALIBUR™ (Becton Dickinson, Mountain View, Calif.). Analysis was performed with CELLQUEST™ software (Becton Dickinson).

Example 6

Mice

Male and female wild-type C57BL/6 mice were purchased from the National Cancer Institute (Frederick, Md.). Age-matched MUC1.Tg mice were obtained using standard breeding methods.

Example 7

Tumor Challenge

On the day of tumor challenge, adherent control and MUC1-expressing B16 tumor cell lines were released from tissue culture flasks by treating with 0.05 mM trypsin and 1.5 mM EDTA in PBS for 5 minutes at 37° C., counted, and resuspended in DMEM at a concentration of $2 \times 10^5$ viable cells/mL. Control and MUC1-expressing Panc02 tumor cell lines were similarly prepared except they were resuspended at $1 \times 10^7$ viable cells/mL. $2 \times 10^4$ viable B16.MUC1, B16.MUC1.CT3, B16.MUC1.CT33, B16.MUC1.CT45, B16.MUC1 (ΔTR), or B16.neo cells were injected subcutaneously, between the scapulae. $1 \times 10^6$ viable Panc02.MUC1, Panc02.MUC1.CT3, Panc02.MUC1.CT33, Panc02.MUC1.CT45, Panc02.MUC1 (ATR), or Panc02.neo were injected subcutaneously, between the scapulae. Tumor growth was evaluated every two to three days, and tumor diameter was measured using a caliper. Kaplan-Meier survival curves were prepared for tumor challenge studies. Death was defined as the date on which the tumor diameter measured 10 mm. Mice were euthanized when the tumor diameter exceeded 10 mm. The log-rank test was used for statistical analyses.

Example 8

Epitope Prediction

Two web-based algorithms were used to analyze the amino acid sequence of MUC1 cytoplasmic tail for potential human and murine MHC class I and class II binding epitopes. The first algorithm, "SYFPEITHI," (Rammensee, et al (1999) supra) was available at www.uni-tuebingen.de/uni/kxi/. This algorithm ranks peptides according to a score taking into account the presence of primary and secondary MHC-binding anchor residues. The second algorithm, "BIMAS," (Parker, et al (1994) supra was available at bimas.dcrt.nih- .gov/molbio/hla_bind/. This algorithm ranks potential binding according to the predicted half-time of dissociation of peptide/MHC complexes.

Example 9

Synthetic Peptides

Peptides used were:

Cys-Gln-Cys-Arg-Arg-Lys-Asn-Tyr-Gly-Gln-Leu-Asp-Ile-Phe-Pro-Ala-Arg-Asp-Thr-Tyr-His-Pro-Met-Ser-Glu-Tyr-Pro-Thr-Tyr-His (SEQ ID NO:47), a 30 amino acid peptide corresponding to MUC1 cytoplasmic tail amino acid residues −3 to 27;

His-Pro-Met-Ser-Glu-Tyr-Pro-Thr-Tyr-His-Thr-His-Gly-Arg-Tyr-Val-Pro-Pro-Ser-Ser-Thr-Asp-Arg-Ser-Pro-Tyr-Glu-Lys-Val-Ser-Ala-Gly (SEQ ID NO:48), a 32 amino acid peptide corresponding to MUC1 cytoplasmic tail amino acid residues to 49, wherein the underlined amino acid residues represent overlapping sequences with peptides of SEQ ID NO:47 and SEQ ID NO:49; and Ser-Thr-Asp-Arg-Ser-Pro-Tyr-Glu-Lys-Val-Ser-Ala-Gly-Asn-Gly-Gly-Ser-Ser-Leu-Ser-Tyr-Thr-Asn-Pro-Ala-Val-Ala-Ala-Ala-Ser-Ala-Asn-Leu (SEQ ID NO:49), a 33 amino acid peptide corresponding to MUC1 cytoplasmic tail amino acid residues 37 to 69.

Additional peptides used include:

His-Ser-Pro-Thr-Met-Asp-Arg-Ser-Glu-Ser-Tyr-Pro-Pro-Tyr-Thr-Glu-Tyr-Lys-His-Ser-Gly-Ala-Val (SEQ ID NO:51), a amino acid peptide corresponding to the scrambled sequence of the overlapping regions peptides of SEQ ID NO:47, SEQ ID NO:48 and SEQ ID NO:49, referred to as control peptide; and a 20 amino acid peptide containing one complete MUC1 tandem repeat (Pro-Asp-Thr-Arg-Pro-Ala-Pro-Gly-Ser-Thr-Ala-Pro-Pro-Ala-His-Gly-Val-Thr-Ser-Ala; SEQ ID NO:50), referred to as TR.

All peptides were synthesized, characterized, and purified to >95% purity by Genemed Synthesis, Inc. (South San Francisco, Calif.).

Example 10

MUC1 Cytoplasmic Tail peptide Vaccinations and Tumor Challenge

Peptides were diluted in PBS, pH 7.4, at a concentration of 500 μg/mL. The mixture was vortexed vigorously for 5 minutes. Mice receiving B16.MUC1 tumors received one vaccination consisting of a combination of 50 μg of peptide of SEQ ID NO:47, 50 μg of peptide of SEQ ID NO:48, and 50 μg of peptide of SEQ ID NO:49 in a total volume of 100 μL by s.c injection between the scapulae. Control mice received one vaccination consisting of 50 μg of control peptide in a total volume of 100 μL by s.c injection between the scapulae or no vaccination. Ten days following vaccination, $2\times10^4$ viable B16.MUC1 cells were injected subcutaneously, between the scapulae. Mice receiving Panc02.MUC1 tumors received three vaccinations, at seven day intervals, consisting of 50 μg of peptide of SEQ ID NO:47 in a total volume of 100 μL by s.c injection between the scapulae. Control mice received three vaccinations, at seven day intervals, consisting of 50 μg of control peptide in a total volume of 100 μL by s.c injection between the scapulae or no vaccination. Ten days following the third vaccination, $1\times10^6$ viable Panc02.MUC1 cells were injected subcutaneously, between the scapulae. Tumor challenge results were evaluated as described herein.

Example 11

Immunohistochemical Examination of Tumors

For immunohistochemical evaluation of MUC1 expression on tumors obtained from vaccinated, control-vaccinated, and nonvaccinated animals, tumor tissue was fixed in a buffered formalin solution (100 mL formalin, 3.4 g $NaH_2PO_4$, and 10.3 g $Na_2HPO_4$)/1000 mL, pH 7.3-7.4, embedded in paraffin and sectioned at a thickness of 5 μm. Tissue sections were assayed using a modification of an ABC immunohistochemical method (Hsu, et al. (1981) *J. Histochem. Cytochem.* 29:577). Briefly, tissue sections were deparaffinized in EZ-DEWAX™ (BioGenex, San Ramon, Calif.). Antigen unmasking was carried out by adding 10 mM citrate buffer and boiling for 10 minutes. The sections were then incubated in blocking serum for 20 minutes and primary monoclonal antibody M2 (Sigma) was added and the samples were kept in a humid chamber at 4° C. overnight. The slides were rinsed with PBS and incubated for 1 hour with biotin-labeled secondary monoclonal antibody. Endogenous peroxidase activity was blocked by incubating the samples in 3% $H_2O_2$ for 5 minutes. The slides were then incubated for 30 minutes at room temperature with ABC reagent (Vector Labs, Burlingame, Calif.). The slides were then rinsed with PBS and incubated for 3-5 minutes with DAB substrate (Vector Labs) observing closely for color to develop. Sections were then incubated for 10 minutes in 50 mM sodium bicarbonate pH 9.6 followed by a 5-second incubation in DAB enhancing solution (Vector Labs) and counterstained with Meyer's hematoxylin for 30 seconds. Cover slips were applied and the slides were examined under a Nikon E400 microscope (Nikon, Tokyo, JP). Images were captured using a Nikon CoolPix 950 digital camera (Nikon).

Example 12

Cytotoxic T Lymphocyte Assay

Detection of MUC1-specific cytotoxic T lymphocytes (CTL) was carried out by generation of effector cells from spleens and lymph nodes (axillary, brachial, inguinal and mesenteric) harvested from vaccinated, control peptide-vaccinated and nonvaccinated mice. Red blood cells were lysed using RBC lysis buffer (800 mg $NH_4Cl$, 80 mg EDTA, 80 mg $NaHCO_3$)/100 mL. EL4 and EL4.MUC1 target cells were labeled with 100 μCi $Na_2{}^{51}CrO_4$ for 1.5 hours and washed. Effector cells were incubated with $5\times10^3$ $^{51}Cr$-labeled EL4 or EL4.MUC1 cells at various effector to target ratios (E:T) in triplicate in 96-well plates (Falcon) in a total volume of 200 μL. The plates were incubated for 6 hours at 37° C. and 5% $CO_2$. Following incubation, 50 μL culture supernatant was transferred to LUMAPLATES™ (Packard Instrument Company, Inc, Meriden, Conn.). The LUMAPLATES™ were air dried overnight at room temperature and radioactivity was measured using a TOPCOUNT® NXT (Packard). Percent specific lysis was determined using the following equation: ((experimental $^{51}Cr$ release−spontaneous $^{51}Cr$ release)/(maximum $^{51}Cr$ release−spontaneous $^{51}Cr$ release))× 100%=% specific lysis. Experimental $^{51}Cr$ release represents $^{51}Cr$ release from targets mixed with effectors, spontaneous $^{51}Cr$ release represents targets in medium only, and maximum $^{51}Cr$ release represents targets lysed with 5% TRITON® X-100.

Example 13

Statistical Analysis

Tumor challenge studies were conducted two or more times. Survival data were pooled and the log-rank test was used for statistical analysis of survival. Additionally, the Cox regression analysis was used to confirm statistical differences among experimental groups and to verify that data from repeated experiments was statistically similar prior to being pooled. For CTL assays, statistical significance was determined by one-way ANOVA followed by Newman-Keuls Multiple Comparison Test. For all statistical tests, a p value<0.05 was considered to be statistically significant.

What is claimed is:

1. A composition comprising a MUC1 cytoplasmic tail peptide, wherein said MUC1 cytoplasmic tail peptide consists of a 9 to 15 amino acid portion of SEQ ID NO: 49, wherein said MUC1 cytoplasmic tail peptide comprises a sequence selected from the group consisting of SEQ ID NO: 3, SEQ ID NO: 4, SEQ ID NO: 6, SEQ ID NO: 7, SEQ ID NO: 8, SEQ ID NO: 9, SEQ ID NO: 14, SEQ ID NO: 18, SEQ ID NO: 19, SEQ ID NO: 21, SEQ ID NO: 25, SEQ ID NO: 26, SEQ ID NO: 28, SEQ ID NO: 31, SEQ ID NO: 39, SEQ ID NO: 41, and SEQ ID NO: 43.

2. The composition of claim 1, wherein said MUC1 cytoplasmic tail peptide comprises a sequence selected from the group consisting of SEQ ID NO: 3, SEQ ID NO: 7, SEQ ID NO: 21, SEQ ID NO: 25, SEQ ID NO: 28, SEQ ID NO: 39, and SEQ ID NO: 41.

3. The composition of claim 1 further comprising at least one additional MUC1 cytoplasmic tail peptide consists of a 9 to 15 amino acid portion of SEQ ID NO: 1.

4. The composition of claim 3, wherein said additional MUC1 cytoplasmic tail peptide consists of a 9 to 15 amino acid portion of SEQ ID NO: 47.

5. The composition of claim 3, wherein said additional MUC1 cytoplasmic tail peptide consists of a 9 to 15 amino acid portion of SEQ ID NO: 48.

6. The composition of claim 1, wherein said composition comprises more than one of said MUC1 cytoplasmic tail peptides.

7. The composition of claim 1 further comprising a carrier protein.

* * * * *

```
                          SEQUENCE LISTING

<160> NUMBER OF SEQ ID NOS: 51

<210> SEQ ID NO 1
<211> LENGTH: 72
<212> TYPE: PRT
<213> ORGANISM: Homo sapiens

<400> SEQUENCE: 1

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His Thr His
            20                  25                  30

Gly Arg Tyr Val Pro Pro Ser Ser Thr Asp Arg Ser Pro Tyr Glu Lys
        35                  40                  45

Val Ser Ala Gly Asn Gly Gly Ser Ser Leu Ser Tyr Thr Asn Pro Ala
    50                  55                  60

Val Ala Ala Ala Ser Ala Asn Leu
65                  70

<210> SEQ ID NO 2
<211> LENGTH: 9
<212> TYPE: PRT
<213> ORGANISM: Homo sapiens

<400> SEQUENCE: 2

Cys Arg Arg Lys Asn Tyr Gly Gln Leu
1               5

<210> SEQ ID NO 3
<211> LENGTH: 9
<212> TYPE: PRT
<213> ORGANISM: Homo sapiens

<400> SEQUENCE: 3

Val Ser Ala Gly Asn Gly Gly Ser Ser
1               5

<210> SEQ ID NO 4
<211> LENGTH: 9
<212> TYPE: PRT
<213> ORGANISM: Homo sapiens

<400> SEQUENCE: 4

Leu Ser Tyr Thr Asn Pro Ala Val Ala
1               5

<210> SEQ ID NO 5
<211> LENGTH: 9
<212> TYPE: PRT
<213> ORGANISM: Homo sapiens

<400> SEQUENCE: 5

Ser Ala Gly Asn Gly Gly Ser Ser Leu
1               5
```

```
<210> SEQ ID NO 6
<211> LENGTH: 9
<212> TYPE: PRT
<213> ORGANISM: Homo sapiens

<400> SEQUENCE: 6

Ala Val Ala Ala Ala Ser Ala Asn Leu
1               5

<210> SEQ ID NO 7
<211> LENGTH: 10
<212> TYPE: PRT
<213> ORGANISM: Homo sapiens

<400> SEQUENCE: 7

Val Ser Ala Gly Asn Gly Gly Ser Ser Leu
1               5                   10

<210> SEQ ID NO 8
<211> LENGTH: 10
<212> TYPE: PRT
<213> ORGANISM: Homo sapiens

<400> SEQUENCE: 8

Pro Ala Val Ala Ala Ala Ser Ala Asn Leu
1               5                   10

<210> SEQ ID NO 9
<211> LENGTH: 10
<212> TYPE: PRT
<213> ORGANISM: Homo sapiens

<400> SEQUENCE: 9

Leu Ser Tyr Thr Asn Pro Ala Val Ala Ala
1               5                   10

<210> SEQ ID NO 10
<211> LENGTH: 10
<212> TYPE: PRT
<213> ORGANISM: Homo sapiens

<400> SEQUENCE: 10

Phe Pro Ala Arg Asp Thr Tyr His Pro Met
1               5                   10

<210> SEQ ID NO 11
<211> LENGTH: 8
<212> TYPE: PRT
<213> ORGANISM: Homo sapiens

<400> SEQUENCE: 11

Arg Arg Lys Asn Tyr Gly Gln Leu
1               5

<210> SEQ ID NO 12
<211> LENGTH: 8
<212> TYPE: PRT
<213> ORGANISM: Homo sapiens

<400> SEQUENCE: 12

Asp Arg Ser Pro Tyr Glu Lys Val
1               5

<210> SEQ ID NO 13
```

```
<211> LENGTH: 8
<212> TYPE: PRT
<213> ORGANISM: Homo sapiens

<400> SEQUENCE: 13

Ala Arg Asp Thr Tyr His Pro Met
1               5

<210> SEQ ID NO 14
<211> LENGTH: 8
<212> TYPE: PRT
<213> ORGANISM: Homo sapiens

<400> SEQUENCE: 14

Ser Ser Leu Ser Tyr Thr Asn Pro
1               5

<210> SEQ ID NO 15
<211> LENGTH: 9
<212> TYPE: PRT
<213> ORGANISM: Homo sapiens

<400> SEQUENCE: 15

Cys Arg Arg Lys Asn Tyr Gly Gln Leu
1               5

<210> SEQ ID NO 16
<211> LENGTH: 9
<212> TYPE: PRT
<213> ORGANISM: Homo sapiens

<400> SEQUENCE: 16

Ser Glu Tyr Pro Thr Tyr His Thr His
1               5

<210> SEQ ID NO 17
<211> LENGTH: 9
<212> TYPE: PRT
<213> ORGANISM: Homo sapiens

<400> SEQUENCE: 17

Ser Leu Ser Tyr Thr Asn Pro Ala Val
1               5

<210> SEQ ID NO 18
<211> LENGTH: 9
<212> TYPE: PRT
<213> ORGANISM: Homo sapiens

<400> SEQUENCE: 18

Tyr Thr Asn Pro Ala Val Ala Ala Ala
1               5

<210> SEQ ID NO 19
<211> LENGTH: 10
<212> TYPE: PRT
<213> ORGANISM: Homo sapiens

<400> SEQUENCE: 19

Ser Tyr Thr Asn Pro Ala Val Ala Ala Ala
1               5                   10

<210> SEQ ID NO 20
<211> LENGTH: 9
<212> TYPE: PRT
<213> ORGANISM: Homo sapiens
```

<400> SEQUENCE: 20

Asp Thr Tyr His Pro Met Ser Glu Tyr
1               5

<210> SEQ ID NO 21
<211> LENGTH: 9
<212> TYPE: PRT
<213> ORGANISM: Homo sapiens

<400> SEQUENCE: 21

Gly Asn Gly Gly Ser Ser Leu Ser Tyr
1               5

<210> SEQ ID NO 22
<211> LENGTH: 9
<212> TYPE: PRT
<213> ORGANISM: Homo sapiens

<400> SEQUENCE: 22

Pro Thr Tyr His Thr His Gly Arg Tyr
1               5

<210> SEQ ID NO 23
<211> LENGTH: 9
<212> TYPE: PRT
<213> ORGANISM: Homo sapiens

<400> SEQUENCE: 23

Asp Ile Phe Pro Ala Arg Asp Thr Tyr
1               5

<210> SEQ ID NO 24
<211> LENGTH: 9
<212> TYPE: PRT
<213> ORGANISM: Homo sapiens

<400> SEQUENCE: 24

Pro Ser Ser Thr Asp Arg Ser Pro Tyr
1               5

<210> SEQ ID NO 25
<211> LENGTH: 10
<212> TYPE: PRT
<213> ORGANISM: Homo sapiens

<400> SEQUENCE: 25

Ala Gly Asn Gly Gly Ser Ser Leu Ser Tyr
1               5                   10

<210> SEQ ID NO 26
<211> LENGTH: 10
<212> TYPE: PRT
<213> ORGANISM: Homo sapiens

<400> SEQUENCE: 26

Ser Thr Asp Arg Ser Pro Tyr Glu Lys Val
1               5                   10

<210> SEQ ID NO 27
<211> LENGTH: 10
<212> TYPE: PRT
<213> ORGANISM: Homo sapiens

<400> SEQUENCE: 27

Asp Ile Phe Pro Ala Arg Asp Thr Tyr His
1               5                   10

<210> SEQ ID NO 28
<211> LENGTH: 10
<212> TYPE: PRT
<213> ORGANISM: Homo sapiens

<400> SEQUENCE: 28

Lys Val Ser Ala Gly Asn Gly Gly Ser Ser
1               5                   10

<210> SEQ ID NO 29
<211> LENGTH: 9
<212> TYPE: PRT
<213> ORGANISM: Homo sapiens

<400> SEQUENCE: 29

Tyr Val Pro Pro Ser Ser Thr Asp Arg
1               5

<210> SEQ ID NO 30
<211> LENGTH: 8
<212> TYPE: PRT
<213> ORGANISM: Homo sapiens

<400> SEQUENCE: 30

Ser Pro Tyr Glu Lys Val Ser Ala
1               5

<210> SEQ ID NO 31
<211> LENGTH: 9
<212> TYPE: PRT
<213> ORGANISM: Homo sapiens

<400> SEQUENCE: 31

Ser Pro Tyr Glu Lys Val Ser Ala Gly
1               5

<210> SEQ ID NO 32
<211> LENGTH: 9
<212> TYPE: PRT
<213> ORGANISM: Homo sapiens

<400> SEQUENCE: 32

Gly Arg Tyr Val Pro Pro Ser Ser Thr
1               5

<210> SEQ ID NO 33
<211> LENGTH: 9
<212> TYPE: PRT
<213> ORGANISM: Homo sapiens

<400> SEQUENCE: 33

Ala Arg Asp Thr Tyr His Pro Met Ser
1               5

<210> SEQ ID NO 34
<211> LENGTH: 9
<212> TYPE: PRT
<213> ORGANISM: Homo sapiens

<400> SEQUENCE: 34

Lys Asn Tyr Gly Gln Leu Asp Ile Phe
1               5

<210> SEQ ID NO 35
<211> LENGTH: 9
<212> TYPE: PRT
<213> ORGANISM: Homo sapiens

<400> SEQUENCE: 35

Gly Gln Leu Asp Ile Phe Pro Ala Arg
1               5

<210> SEQ ID NO 36
<211> LENGTH: 9
<212> TYPE: PRT
<213> ORGANISM: Homo sapiens

<400> SEQUENCE: 36

Arg Arg Lys Asn Tyr Gly Gln Leu Asp
1               5

<210> SEQ ID NO 37
<211> LENGTH: 9
<212> TYPE: PRT
<213> ORGANISM: Homo sapiens

<400> SEQUENCE: 37

His Pro Met Ser Glu Tyr Pro Thr Tyr
1               5

<210> SEQ ID NO 38
<211> LENGTH: 15
<212> TYPE: PRT
<213> ORGANISM: Homo sapiens

<400> SEQUENCE: 38

Arg Lys Asn Tyr Gly Gln Leu Asp Ile Phe Pro Ala Arg Asp Thr
1               5                   10                  15

<210> SEQ ID NO 39
<211> LENGTH: 15
<212> TYPE: PRT
<213> ORGANISM: Homo sapiens

<400> SEQUENCE: 39

Arg Ser Pro Tyr Glu Lys Val Ser Ala Gly Asn Gly Gly Ser Ser
1               5                   10                  15

<210> SEQ ID NO 40
<211> LENGTH: 15
<212> TYPE: PRT
<213> ORGANISM: Homo sapiens

<400> SEQUENCE: 40

Leu Asp Ile Phe Pro Ala Arg Asp Thr Tyr His Pro Met Ser Glu
1               5                   10                  15

<210> SEQ ID NO 41
<211> LENGTH: 15
<212> TYPE: PRT
<213> ORGANISM: Homo sapiens

<400> SEQUENCE: 41

Tyr Glu Lys Val Ser Ala Gly Asn Gly Gly Ser Ser Leu Ser Tyr
1               5                   10                  15

<210> SEQ ID NO 42
<211> LENGTH: 15

```
<212> TYPE: PRT
<213> ORGANISM: Homo sapiens

<400> SEQUENCE: 42

Gly Arg Tyr Val Pro Pro Ser Ser Thr Asp Arg Ser Pro Tyr Glu
1               5                   10                  15

<210> SEQ ID NO 43
<211> LENGTH: 15
<212> TYPE: PRT
<213> ORGANISM: Homo sapiens

<400> SEQUENCE: 43

Gly Ser Ser Leu Ser Tyr Thr Asn Pro Ala Val Ala Ala Ala Ser
1               5                   10                  15

<210> SEQ ID NO 44
<211> LENGTH: 15
<212> TYPE: PRT
<213> ORGANISM: Homo sapiens

<400> SEQUENCE: 44

Tyr Gly Gln Leu Asp Ile Phe Pro Ala Arg Asp Thr Tyr His Pro
1               5                   10                  15

<210> SEQ ID NO 45
<211> LENGTH: 15
<212> TYPE: PRT
<213> ORGANISM: Homo sapiens

<400> SEQUENCE: 45

Tyr His Pro Met Ser Glu Tyr Pro Thr Tyr His Thr His Gly Arg
1               5                   10                  15

<210> SEQ ID NO 46
<211> LENGTH: 15
<212> TYPE: PRT
<213> ORGANISM: Homo sapiens

<400> SEQUENCE: 46

Tyr Pro Thr Tyr His Thr His Gly Arg Tyr Val Pro Pro Ser Ser
1               5                   10                  15

<210> SEQ ID NO 47
<211> LENGTH: 30
<212> TYPE: PRT
<213> ORGANISM: Artificial Sequence
<220> FEATURE:
<223> OTHER INFORMATION: Synthetic peptide

<400> SEQUENCE: 47

Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His
            20                  25                  30

<210> SEQ ID NO 48
<211> LENGTH: 32
<212> TYPE: PRT
<213> ORGANISM: Artificial Sequence
<220> FEATURE:
<223> OTHER INFORMATION: Synthetic peptide

<400> SEQUENCE: 48

His Pro Met Ser Glu Tyr Pro Thr Tyr His Thr His Gly Arg Tyr Val
1               5                   10                  15
```

```
Pro Pro Ser Ser Thr Asp Arg Ser Pro Tyr Glu Lys Val Ser Ala Gly
            20                  25                  30

<210> SEQ ID NO 49
<211> LENGTH: 33
<212> TYPE: PRT
<213> ORGANISM: Artificial Sequence
<220> FEATURE:
<223> OTHER INFORMATION: Synthetic peptide

<400> SEQUENCE: 49

Ser Thr Asp Arg Ser Pro Tyr Glu Lys Val Ser Ala Gly Asn Gly Gly
1               5                   10                  15

Ser Ser Leu Ser Tyr Thr Asn Pro Ala Val Ala Ala Ala Ser Ala Asn
            20                  25                  30

Leu

<210> SEQ ID NO 50
<211> LENGTH: 20
<212> TYPE: PRT
<213> ORGANISM: Artificial Sequence
<220> FEATURE:
<223> OTHER INFORMATION: Synthetic peptide

<400> SEQUENCE: 50

Pro Asp Thr Arg Pro Ala Pro Gly Ser Thr Ala Pro Pro Ala His Gly
1               5                   10                  15

Val Thr Ser Ala
            20

<210> SEQ ID NO 51
<211> LENGTH: 23
<212> TYPE: PRT
<213> ORGANISM: Artificial Sequence
<220> FEATURE:
<223> OTHER INFORMATION: Synthetic peptide

<400> SEQUENCE: 51

His Ser Pro Thr Met Asp Arg Ser Glu Ser Tyr Pro Pro Tyr Thr Glu
1               5                   10                  15

Tyr Lys His Ser Gly Ala Val
            20
```